United States Patent
Quaranta-Guido

(10) Patent No.: US 9,513,173 B2
(45) Date of Patent: Dec. 6, 2016

(54) METHOD FOR CONTROLLING INTERIOR VEHICLE TEMPERATURE TO PROTECT OCCUPANTS FROM EXTREME HEAT

(71) Applicant: Sandra Quaranta-Guido, Lake Hopatcong, NJ (US)

(72) Inventor: Sandra Quaranta-Guido, Lake Hopatcong, NJ (US)

( * ) Notice: Subject to any disclaimer, the term of this patent is extended or adjusted under 35 U.S.C. 154(b) by 11 days.

(21) Appl. No.: 14/487,620

(22) Filed: Sep. 16, 2014

(65) Prior Publication Data
US 2016/0075210 A1   Mar. 17, 2016

(51) Int. Cl.
| | | |
|---|---|---|
| B60R 22/00 | (2006.01) |
| E05F 15/00 | (2015.01) |
| G05D 1/00 | (2006.01) |
| G05D 3/00 | (2006.01) |
| G06F 7/00 | (2006.01) |
| G06F 17/00 | (2006.01) |
| G06F 7/70 | (2006.01) |
| G01K 1/02 | (2006.01) |
| B60Q 9/00 | (2006.01) |
| G01S 19/13 | (2010.01) |
| G01N 33/00 | (2006.01) |
| B60H 1/00 | (2006.01) |

(52) U.S. Cl.
CPC ........... *G01K 1/024* (2013.01); *B60H 1/00778* (2013.01); *B60Q 9/00* (2013.01); *G01N 33/004* (2013.01); *G01S 19/13* (2013.01)

(58) Field of Classification Search
CPC .................................................. B60H 1/00735
See application file for complete search history.

(56) References Cited

U.S. PATENT DOCUMENTS

| | | | |
|---|---|---|---|
| 6,496,106 B1 | 12/2002 | Rodriguez | |
| 7,081,811 B2 | 7/2006 | Johnston et al. | |
| 2003/0098784 A1* | 5/2003 | Van Bosch | B60R 25/1004 340/425.5 |
| 2005/0061563 A1* | 3/2005 | Syed | B60K 6/48 180/65.25 |
| 2006/0179853 A1* | 8/2006 | Vosburgh | B60H 1/00742 62/126 |

\* cited by examiner

*Primary Examiner* — Imran Mustafa
(74) *Attorney, Agent, or Firm* — Maier & Maier, PLLC

(57) ABSTRACT

A method for protecting occupants of in passenger compartment of a parked motor vehicle from exposure to dangerously elevated temperatures is based on control of vehicle systems by a central microprocessor in communication with $CO_2$ and temperature sensors and a wireless communication module. The method implements a graduated, progressive series of warnings and responses as the cabin temperature reaches certain designated setpoints, so that security-compromising steps, such as opening windows, can be deferred until less extreme measures have been exhausted.

7 Claims, 2 Drawing Sheets

METHOD FOR CONTROLLING INTERIOR VEHICLE TEMPERATURE TO PROTECT OCCUPANTS FROM EXTREME HEAT

FIELD OF INVENTION

The present invention relates to the field of systems for monitoring and controlling the climate in a passenger compartment of a motor vehicle, and more particularly to systems for preventing the over-heating of an occupied passenger compartment of a parked motor vehicle.

BACKGROUND OF THE INVENTION

Due to the greenhouse effect, life-threatening temperatures can develop very rapidly inside the passenger cabin of a parked motor vehicle when ambient temperatures exceed 75° F. Animals and small children confined in a car with the windows closed will succumb to heat exhaustion in a matter of minutes as the cabin temperature exceeds 110° F. Deaths of children and pets from heat exposure in parked vehicles are recurring tragedies that can be avoided with suitable prevention systems. The development of advanced central microprocessor systems capable of monitoring and controlling all vehicle systems in newer vehicles provides a means by which cabin temperatures can be monitored and maintained within a safe range.

The need to respond rapidly to cabin over-heating in an occupied parked vehicle must be balanced, however, with the need to preserve the security of the occupants, who are often infants and pets. For example, immediately opening windows and unlocking doors when a temperature increase is detected may leave an infant exposed to abduction or enable a pet to escape. Therefore, there is a need for a system which implements a graduated, progressive series of warnings and responses as the cabin temperature reaches certain designated setpoints, so that security-compromising steps can be deferred until less extreme measures have been exhausted.

SUMMARY OF THE INVENTION

The present invention is a method for protecting occupants in a passenger compartment of a parked motor vehicle from exposure to dangerously elevated temperatures. To implement this method, the vehicle must be equipped with a central microprocessor, or equivalent central CPU or computer system, which is capable of monitoring the status of and controlling the operations of the major vehicle systems, including engine, power train, electrical (including batteries), climate controls (including fans), windows, doors, horns, alarms, lights, and navigation (including GPS).

The vehicle must also be equipped with multiple carbon dioxide ($CO_2$) sensors and temperature sensors. These sensors should be distributed within the passenger compartment so as to monitor cabin conditions and generate representative data on $CO_2$ concentration and temperature. These sensors have interfaces with the central microprocessor, which controls sensor operations and receives the $CO_2$ and temperature data generated by the sensors.

The vehicle is also equipped with a wireless communication module, also having an interface with the central microprocessor, which controls its operations so that wireless warning messages can be sent to designated contacts.

A $CO_2$ concentration indicative of the presence of one or more occupants in the passenger compartment is determined and is stored in the central microprocessor. Also established and stored in the central microprocessor are a progressive series of emergency response temperature setpoints, comprising a lowest first temperature setpoint, a maximum temperature setpoint, and one or more intermediate temperature setpoints between the first temperature setpoint and the maximum temperature setpoint.

For example, there can be three programmed emergency response temperature setpoints, based on a maximum temperature setpoint of 110° F., with the first temperature setpoint at 80% of the maximum, or 88° F., and the second temperature setpoint at 90% of the maximum, or 99° F.

A progressive series of emergency warning messages and emergency response actions are formulated and stored in the central microprocessor. For each emergency response temperature setpoint there are one or more corresponding warning messages and one or more corresponding response actions. Hence, in the example cited above, there would be a set of initial warning messages and initial response actions to be implemented when the cabin temperature reaches the first setpoint of 88° F., and a set of interim warning messages and interim response actions to be implemented when the cabin temperature reaches the second setpoint of 99° F., and a set of final warning messages and final response actions to be implemented when the cabin temperature reaches the maximum setpoint of 110° F.

The $CO_2$ sensors are activated when the central microprocessor determines, based on its monitoring of the status of vehicle systems, such as the engine, the drive train and the climate control system, that the vehicle is parked and the climate control system is not operating. The central microprocessor then compares the generated $CO_2$ concentration data with the established activation $CO_2$ concentration level, and when that level is equaled or exceeded, it activates the temperature sensors, which generate temperature data for the passenger compartment.

The central microprocessor next compares the generated temperature data with the emergency response temperature setpoints. When each temperature setpoint is equaled or exceeded, the corresponding warning messages are sent to corresponding designated contacts through the wireless communications module, and the central microprocessor implements the initial response actions through one or more of the vehicle systems.

Referring to our previous example, when the cabin temperature reaches the first setpoint of 88° F., the vehicle owner and his/her family members could be notified by text messages, and one or more fans could be activated to circulate ambient air through the passenger compartment. Then, when the cabin temperature reaches the second setpoint of 99° F., a second warning message could be sent to the owner and his/her family, and the central emergency microprocessor could also send a 911 emergency text or call, including GPS coordinates for the vehicle location. The central microprocessor could also activate some or all of the vehicle's climate control features, such as air-conditioning, initially on battery power, but switching to engine power when the battery has discharged below a designated level. Finally, when the cabin temperature reaches the allowed maximum of 110° F., a third series of warning messages, including emergency/911 messages with GPS coordinates, could be sent, and the central microprocessor could implement final response actions, such as opening windows, unlocking doors, sounding alarms, and flashing emergency lights.

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope either of the foregoing summary description or of the claims which follow.

DETAILED DESCRIPTION OF THE PREFERRED EMBODIMENT

Figure 1:
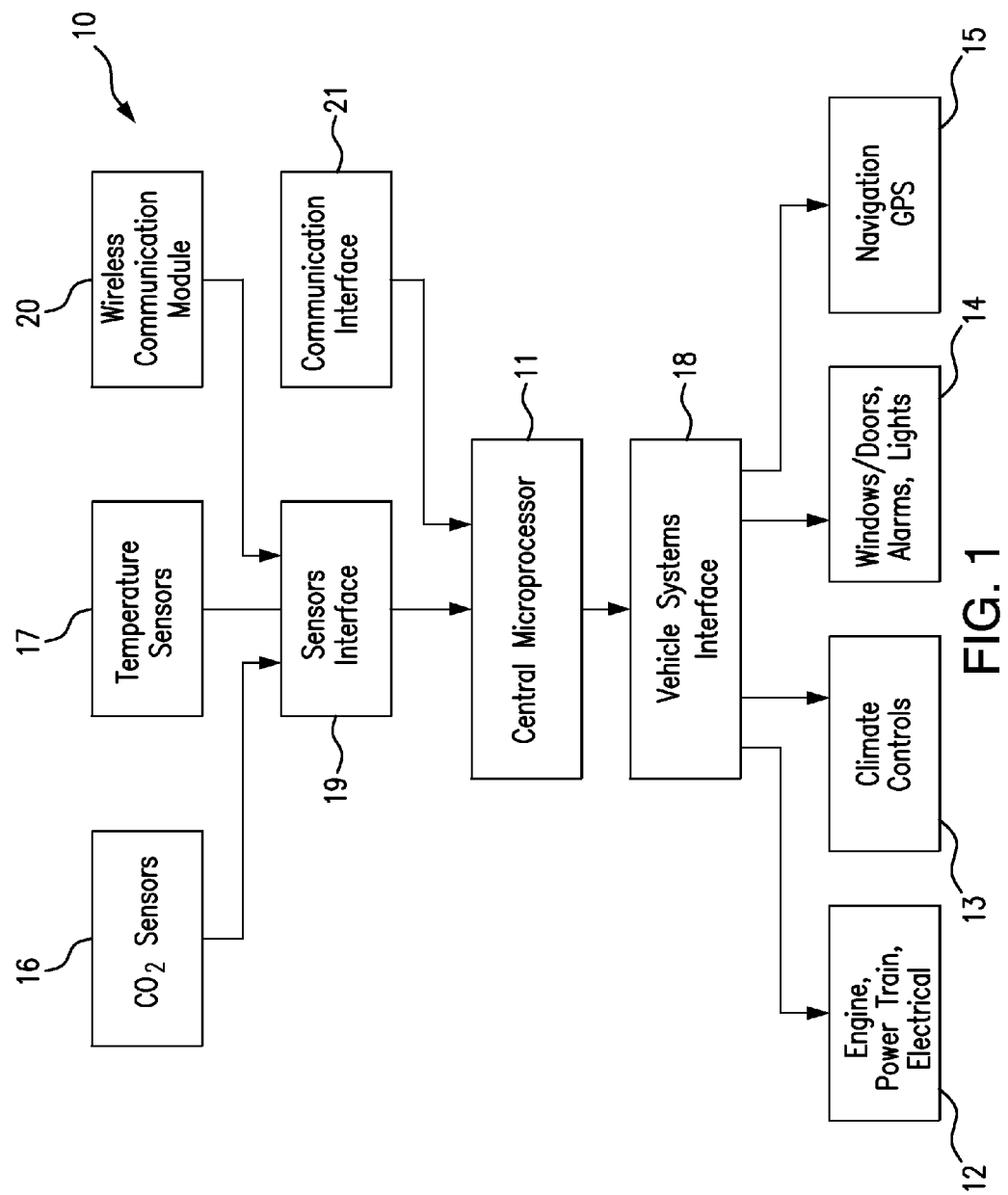
FIG. 1 is a schematic diagram of the control, sensor, interface and communication features of one embodiment of the present invention.

FIG. 1 schematically depicts the vehicle equipment required to implement one embodiment of the passenger compartment temperature protection method of the present invention 10. A central microprocessor 11 monitors and controls multiple vehicle systems, including engine, power train and electrical systems 12, climate control systems 13, window, door, alarm and light systems 14, and navigation/GPS systems 15, through a vehicle systems interface 18.

The central microprocessor also controls and monitors multiple $CO_2$ sensors 16 and temperature sensors 17, through a sensors interface 19. Wireless messages, as text or voice, are sent by the central microprocessor 11 through a communication interface 12 to a wire communication module 21.

Figure 2:
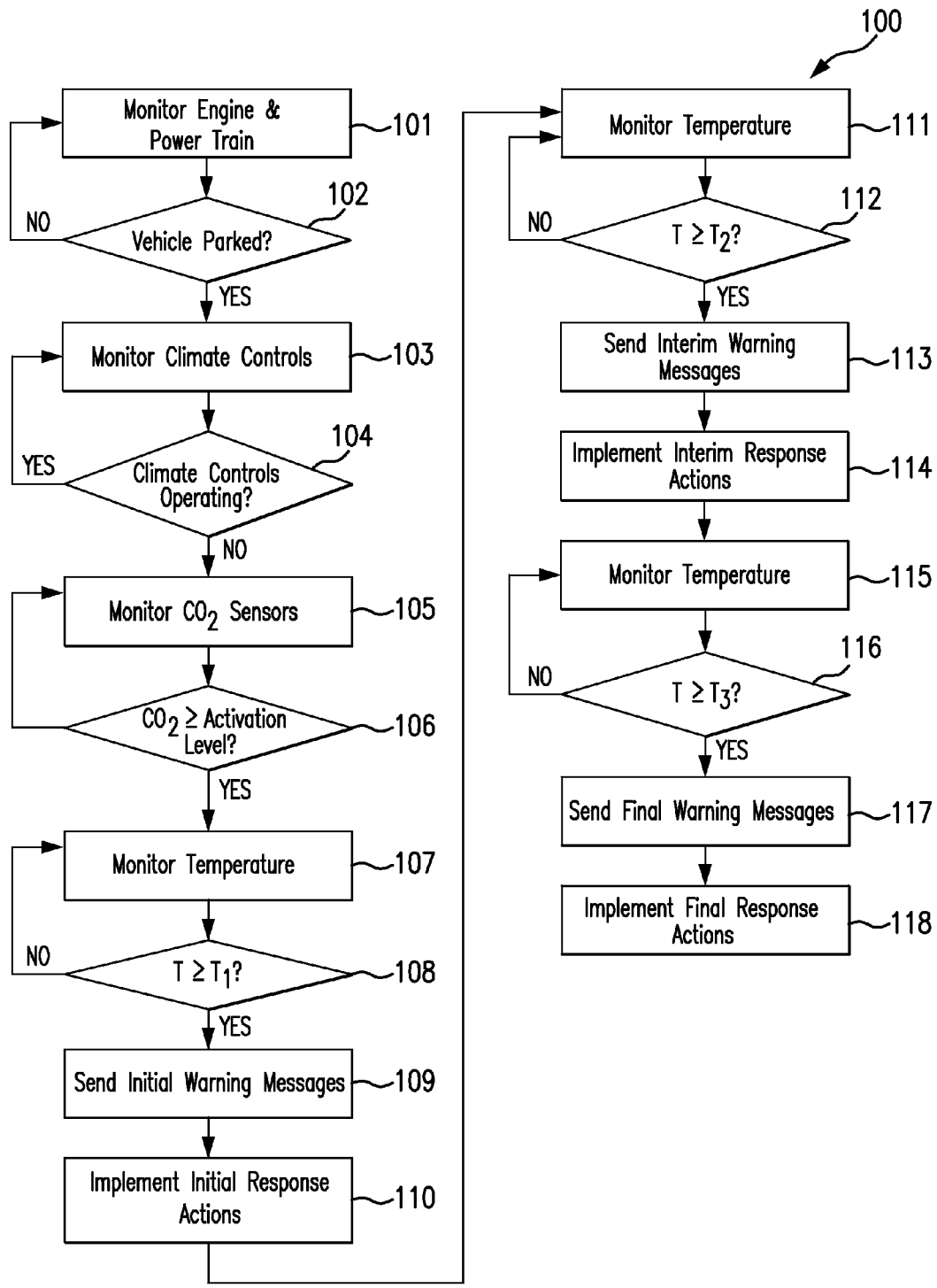
FIG. 2 is a flow chart depicting the method steps of one embodiment of the present invention.

FIG. 2 depicts the sequence of steps comprising an exemplary embodiment of the present invention 100. The central microprocessor 11 monitors the engine and power train 101 to determine if the vehicle is parked 102. If so, the central microprocessor 11 also monitors the climate controls 103 to determine if they are operating 104. If not, the central microprocessor 11 monitors the $CO_2$ sensors 104 and compares the $CO_2$ concentration readings for the passenger compartment with an activation level indicative of the presence of occupants 106. If occupancy is detected, the central microprocessor 11 monitors cabin temperature 107 and compares it with the lowest established emergency response temperature setpoint, designated in FIG. 2 as $T_1$ 108. If the first temperature setpoint is equaled or exceeded, initial warning messages are sent 109 and initial response actions are implemented 110.

The central microprocessor 11 then continues to monitor cabin temperatures 111, comparing it to the next lowest established emergency response temperature setpoint 112, designated as $T_2$ in FIG. 2. If the second temperature setpoint is equaled or exceeded, interim warning messages are sent 113 and interim response actions are implemented 114. The temperature monitoring continues 115, until the highest established emergency response temperature $T_3$ is equaled or exceeded 116, at which point the central microprocessor 11 sends the final warning messages 117 and implements the final response actions 118.

Although the preferred embodiment of the present invention has been disclosed for illustrative purposes, those skilled in the art will appreciate that many additions, modifications and substitutions are possible, without departing from the scope and spirit of the present invention as defined by the accompanying claims.

What is claimed is:

1. A method for protecting occupants of a passenger compartment of a parked motor vehicle, comprising:
    (a) equipping the vehicle with a central microprocessor, which monitors the status of and controls the operation of multiple vehicle systems, including an engine, a power train, one or more batteries, a climate control system, multiple windows, multiple doors, one or more sound-producing devices, and one or more emergency lights;
    (b) equipping the vehicle with one or more carbon dioxide ($CO_2$) sensors, which are controlled by the central microprocessor and which monitor the concentration of $CO_2$ in the passenger compartment and generate $CO_2$ concentration data;
    (c) equipping the vehicle with one or more temperature sensors, which are controlled by the central microprocessor and which monitor the temperature in the passenger compartment and generate temperature data;
    (d) equipping the vehicle with a wireless communication module, which is controlled by the central microprocessor and which sends and receives wireless messages;
    (e) providing one or more interfaces between the central microprocessor and the $CO_2$ sensors, the temperature sensors and the wireless communication module, wherein the interfaces transmit the $CO_2$ concentration data, the temperature data and wireless messages to the central microprocessor and enable the central microprocessor to direct the wireless communications module to send wireless messages;
    (f) establishing and storing in the central microprocessor an activation $CO_2$ concentration level, which is indicative of the presence of one or more occupants in the passenger compartment;
    (g) establishing and storing in the central microprocessor a progressive series of emergency response temperature setpoints, comprising a first temperature setpoint, a maximum temperature setpoint, and one or more intermediate temperature setpoints between the first temperature setpoint and the maximum temperature set point;
    (h) formulating and storing in the central microprocessor a graduated, progressive sequence of emergency warning messages and emergency response actions, comprising one or more warning messages and one or more response actions, corresponding to each of the emergency response temperature setpoints, so as to comprise one or more initial warning messages and one or more initial response actions, corresponding to the first temperature setpoint, one more final warning messages and one or more final response actions, corresponding to the maximum temperature setpoint, and one or more interim warning messages and one or more interim response actions, corresponding to each of the intermediate temperature setpoints;
    (i) activating the $CO_2$ sensors when the central microprocessor determines, based on the status of one or more monitored vehicle systems by the microprocessor's monitoring the engine, the power train, and the climate control system, that the vehicle is parked and that the climate control system is not operating regardless of the presence of an occupant;
    (j) using the central microprocessor to compare the $CO_2$ concentration data with the activation $CO_2$ concentration level to determine if at least an occupant is present based on a comparison of a $CO_2$ concentration level indicative to a presence of at least an occupant in the vehicle which is stored in the central microprocessor to a $CO_2$ level measured by the $CO_2$ sensors only after the central microprocessor determines that the vehicle is parked and the climate control system is not operating;

(k) when the $CO_2$ concentration data equals or exceeds the activation $CO_2$ concentration level, determining an occupant is present in the passenger compartment and causing the central microprocessor to activate the temperature sensors;

(l) using the central microprocessor to compare the temperature data generated by the temperature sensors with the emergency response temperature setpoints;

(m) when the central microprocessor determines that the temperature data equals or exceeds the first temperature setpoint, causing the central microprocessor to transmit, through the wireless communication module, the initial warning messages to one or more designated initial contacts, and causing the central microprocessor to implement the initial response actions;

(n) when the central microprocessor determines that the temperature data equals or exceeds one of the intermediate temperature setpoints, causing the central microprocessor to transmit, through the wireless communication module, the corresponding interim warning messages to one or more designated interim contacts, and causing the central microprocessor to implement the corresponding interim response actions; and (o) when the central microprocessor determines that the temperature data equals or exceeds the maximum temperature setpoint, causing the central microprocessor to transmit, through the wireless telecommunication module, the final warning messages to one or more designated final contacts, and causing the central microprocessor to implement the final response actions.

2. The method of claim 1, wherein emergency response actions having the effect of compromising the security of the motor vehicle and/or the security of the occupants, including opening the windows and unlocking the doors, are deferred to the final response actions.

3. The method of claim 2, wherein the climate control system includes one or more fans, which circulate ambient air through the passenger compartment, and wherein the initial response actions include activation of one or more of the fans.

4. The method of claim 3, wherein the climate control system includes one or more air-conditioning units, which control the temperature in the passenger compartment, and wherein the interim response actions include activation of one or more of the air-conditioning units.

5. The method of claim 4, further comprising the additional steps of equipping the vehicle with a GPS module, which receives satellite GPS coordinates of the location of the vehicle and has an interface with the central microprocessor, and causing the central microprocessor to transmit the GPS coordinates of the vehicle's location through the wireless communication module to one or more police and emergency contacts as part of the interim warning messages and the final warning messages.

6. The method of claim 5, wherein the final response actions include activating one or more of the vehicle's emergency lights and one or more of the vehicle's sound-producing devices.

7. The method of claim 6, further comprising the additional step of causing the central microprocessor to start the engine when the batteries are discharged below a designated level.

\* \* \* \* \*